United States Patent
Shi et al.

(10) Patent No.: US 10,617,649 B2
(45) Date of Patent: Apr. 14, 2020

(54) PREPARATION METHOD OF AZACITIDINE FOR INJECTION

(71) Applicant: Zhejiang Huahai Pharmaceutical Co., Ltd, Xunqiao, Linhai, Zhejiang (CN)

(72) Inventors: Xiangjie Shi, Zhejiang (CN); Jiening Liu, Zhejiang (CN); Xinshi Wang, Zhejiang (CN); Libin Hu, Zhejiang (CN); Hao Chen, Zhejiang (CN); Zhiyun Wang, Zhejiang (CN)

(73) Assignee: Zhejiang Huahai Pharmaceutical Co., Ltd., Linhai, Zhejiang (CN)

( * ) Notice: Subject to any disclaimer, the term of this patent is extended or adjusted under 35 U.S.C. 154(b) by 0 days.

(21) Appl. No.: 16/086,592

(22) PCT Filed: Mar. 17, 2017

(86) PCT No.: PCT/CN2017/077026
§ 371 (c)(1),
(2) Date: Sep. 19, 2018

(87) PCT Pub. No.: WO2017/162103
PCT Pub. Date: Sep. 28, 2017

(65) Prior Publication Data
US 2019/0133953 A1    May 9, 2019

(30) Foreign Application Priority Data

Mar. 24, 2016 (CN) .......................... 2016 1 0172614

(51) Int. Cl.
| | |
|---|---|
| *A61K 9/19* | (2006.01) |
| *A61K 31/706* | (2006.01) |
| *F26B 5/06* | (2006.01) |
| *A61K 47/26* | (2006.01) |
| *A61K 9/00* | (2006.01) |
| *A61K 47/10* | (2017.01) |

(52) U.S. Cl.
CPC .............. *A61K 9/19* (2013.01); *A61K 9/0019* (2013.01); *A61K 31/706* (2013.01); *A61K 47/10* (2013.01); *A61K 47/26* (2013.01); *F26B 5/06* (2013.01)

(58) Field of Classification Search
None
See application file for complete search history.

(56) References Cited

U.S. PATENT DOCUMENTS

| 9,765,108 B2* | 9/2017 | Shivakumar ........... A61K 45/06 |
| 2008/0113424 A1* | 5/2008 | Koyanagi ........ C07K 14/43531 435/272 |
| 2011/0042247 A1* | 2/2011 | Kocherlakota ...... A61K 9/0019 206/223 |
| 2015/0374731 A1* | 12/2015 | Maio .................. A61K 31/7068 424/174.1 |

FOREIGN PATENT DOCUMENTS

| CN | 103338753 A | 1/2011 |
| CN | 105769775 A | 3/2016 |

OTHER PUBLICATIONS

Dover, G. J., Charache, S., Boyer, S. H., Vogelsang, G., & Moyer, M. (1985). 5-Azacytidine increases HbF production and reduces anemia in sickle cell disease: dose-response analysis of subcutaneous and oral dosage regimens. Blood, 66(3), 527-532. (Year: 1985).*

* cited by examiner

Primary Examiner — Dale R Miller
(74) Attorney, Agent, or Firm — Umberg Zipser LLP

(57) ABSTRACT

Disclosed is a preparation method for an azacitidine for injection, wherein each injection vial of azacitidine for injection contains 100 mg of azacitidine and 100 mg of mannitol. The preparation method comprises the steps of measuring 80% of the total volume of water for injection at a temperature of 2-6° C.; adding mannitol, and stirring to completely dissolved at a temperature of 2-6° C.; adding azacitidine, stirring to completely dissolved at a temperature of 2-6° C. to obtain an azacitidine solution for injection; filling each injection vial with 23 ml azacitidine solution for injection after filtration; freeze-drying at a preset temperature; and stoppering, capping and packaging after nitrogen filling. The preparation method has the advantages of a simple process, low energy consumption, high production efficiency and stable product quality.

7 Claims, No Drawings

PREPARATION METHOD OF AZACITIDINE FOR INJECTION

This application claims the priority of Chinese Patent Application No. 201610172614.7, with the title of "PREPARATION METHOD OF AZACITIDINE FOR INJECTION", filed on Mar. 24, 2016 before the State Intellectual Property Office of China, which is incorporated herein by reference in its entirety.

FIELD OF THE INVENTION

The present invention relates to the field of medical technology, in particular to a preparation method of azacitidine for injection.

BACKGROUND OF THE INVENTION

Myelodysplastic syndrome (MDS) is a group of diseases characterized by clonal abnormalities in hematopoietic stem cells that cause hematopoietic function failure and a high risk of progression to acute myeloid leukemia (AML). The disease is divided into five types, namely, refractory anemia (RA), ring-shaped sideroblastic anemia, refractory anemia with excess of blasts (RAEB), refractory anemia with excess of blasts in transformation (RAEB-T) and chronic myelomonocytic leukemia (CMML).

In Europe and America, the incidence of MDS is 4 per 100,000 each year, which is twice the incidence of AML. In the elderly population over 70 years old, the incidence of MDS can reach 20 per 100,000. In China, the incidence of this disease has increased due to the extension of the average life expectancy and the aging of the population. Generally, the supportive therapy is used to control the progression of the disease in patients with low risk of MDS, while effective medicaments or therapies are needed for the treatment of patients with high risk of MDS due to poor prognosis.

Azacitidine is a DNA methyltransferase inhibitor that can cause DNA hypomethylation and has a direct cytotoxicity, developed by Pharmion Pharmaceuticals, USA. In May 2004, the US FDA approved the drug Vidaza for marketing for the treatment of all subtypes of MDS. Due to the rapid hydrolysis of the active ingredient azacitidine in water, the substances related to the lyophilized preparation are difficult to control, and the stability of the product during storage is poor, which has a potential impact on the safety and efficacy of clinical medication.

Patent CN103251564A discloses an azacitidine for injection and the preparation method thereof, which mainly controls the pH value of aqueous solution of azacitidine by using hydrochloric acid or sodium hydroxide and reduces related substances of the product after lyophilization. However, in the preparation process of the present invention, it is necessary to add activated carbon and keep the temperature at 80° C. in a water bath for 20 minutes, and then removing the activated carbon by filtration. It is well known that activated carbon tends to leak and remain during filtration, brings a potential safety risk. Therefore, it is still necessary to provide a method with a simple process and stable quality.

Patent CN101632643A discloses an azacitidine for injection and the preparation method thereof, which attempts to increase the stability of the product in aqueous solution by using vitamin C as a stabilizer. However, activated carbon still needs to be added in the preparation process, and thus leakage and residue problems of the activated carbon during filtration cannot be avoided. In addition, vitamin C is a component that not included in the original product, and the introduction of a new component may cause an unnecessary safety problem for the injection.

Patent US20110042247 discloses a preparation method of azacitidine for injection, comprising 1) cooling 95% sterile water to −1 to −3° C.; 2) adding mannitol and stirring to dissolve; 3) adding azacitidine with the desired quality and stirring the mixture to form a solution; 4) controlling the final temperature at −3° C. and stirring for 5 minutes until the solution is clear; 5) filtering the solution through a 0.2 μm sterile filter; 6) bottling and lyophilizing. It is well known that circulating condensed water is commonly used in production at present, and it is impossible to perform circulating cooling since water is easily crystallized at −1 to −3° C. Therefore, it is often necessary to replace a cooling solvent such as absolute ethanol, which often brings danger to production and increases production cost since absolute ethanol is flammable and explosive.

Therefore, it is still necessary to provide a new solution to overcome the above disadvantages, such that the azacitidine for injection has a simple process for production and qualified quality, and is beneficial to commercial production.

SUMMARY OF THE INVENTION

The inventors have found from researches that when the bacterial endotoxin in raw materials and excipients is well controlled, it is not necessary to add activated carbon to adsorb and remove the pyrogen during the preparation process, and the bacterial endotoxin in the produced azacitidine for injection still meets quality requirements.

Reduction of activated carbon adsorption step during the preparation of azacitidine for injection can not only reduce the process steps in the production process, but also improve production efficiency. Adsorption and removal of pyrogen by activated carbon generally requires continuous stirring at a temperature of 60° C. or higher, while the solution of azacitidine to be added is strictly controlled at 2-6° C. Therefore, it is necessary to cool the solution to 2-6° C. after removing the pyrogen through condensed water in a liquid tank jacket before adding the raw material azacitidine. Theoretically the minimum temperature of condensed water is close to 0° C. It takes a long time to reduce the solution after removing the pyrogen from a high temperature to 2-6° C. by condensed water (0° C.), which not only causes an increase in energy consumption but also affects production efficiency.

The inventors have found from researches that azacitidine has good stability when the temperature for preparing azacitidine solution is controlled at 2-6° C. When the temperature of azacitidine solution is higher than 6° C., the content of azacitidine can be significantly decreased, and the related substances are significantly increased, resulting in a decrease in product quality.

The inventors have found from researches that azacitidine has the same stability when the temperature for preparing azacitidine solution is controlled at 4-6° C. compared to the temperature being controlled at 2-3° C. Also, the temperature of 4-6° C. is conducive to increase production efficiency and reduce energy consumption. At present, the control of solution temperature is mainly performed by decreasing the temperature of water for injection to a target range with condensed water and then keeping the temperature through the condensed water circulating in the liquid tank. Condensed water is in a state of solid-liquid coexistence, and is impossible to keep the temperature by flow circulation when the condensed water is close to its lowest temperature of 0° C. Therefore, in order to maintain the circulation state, the temperature of condensed water is often controlled at 1-3° C. Controlling the temperature of the solution at 2-4° C. with condensed water of 1-3° C. often requires a longer cooling time while the ambient temperature in the production area is controlled at 18-26° C. Lower temperature of the solution often requires more energy consumption for temperature preservation and thus increases production costs. Therefore, when the temperature for preparing the azacitidine solution is controlled at 4-6° C., the production efficiency is higher, the cost is reduced, and the quality of the product is more stable.

The invention provides a preparation method for azacitidine for injection, wherein each injection vial of azacitidine for injection comprises 100 mg of azacitidine and 100 mg of mannitol, the preparation method comprises following steps:
a. measuring 80% of the total volume of water for injection at a temperature of 2-6° C.;
b. adding mannitol, stirring to completely dissolved at a temperature of 2-6° C.;
c. adding azacitidine, stirring to completely dissolved at a temperature of 2-6° C. to obtain an azacitidine solution for injection;
d. filling each injection vial with 23 ml azacitidine solution for injection after filtration;
e. freeze-drying at a preset temperature; and
f. stoppering, capping and packaging after nitrogen filling.

The invention provides a preparation method of azacitidine for injection, wherein the preparation method does not comprise a step of adsorbing with an activated carbon.

The invention provides a preparation method for azacitidine for injection, wherein the azacitidine has a content of ≤0.6 Eu/mg of bacterial endotoxin.

The invention provides a preparation method for azacitidine for injection, wherein the mannitol has a content of ≤2.5 Eu/g of bacterial endotoxin.

The invention provides a preparation method for azacitidine for injection, wherein a prepared product of azacitidine for injection has a content of ≤1.2 Eu/mg of bacterial endotoxin.

The invention provides a preparation method for azacitidine for injection, wherein the temperature for preparing a solution is more preferably controlled at 4-6° C.

The invention provides a preparation method for azacitidine for injection, wherein the freeze-drying step comprises:
a. pre-freezing step: placing a sample into a shelf after a temperature of the shelf is reduced to −35±5° C. and maintaining the temperature for 2 hours;
b. first sublimation drying step: reducing vacuum degree to 50-150 Oar, raising the temperature of the shelf to −10° C. at a rate of 15° C./h, and maintaining the temperature for 15 hours; and
c. second sublimation drying step: maintaining vacuum degree to 50-150 Oar, raising the temperature of the shelf to 30° C. at a rate of 20° C./h, maintaining the temperature for 18 hours, stoppering after nitrogen filling, and taking out from a freeze-drier.

The invention provides a greatly shortened freeze-drying cycle compared with the prior art, which is beneficial to improve production efficiency and reduce energy consumption.

According to the present invention, the preparation method of azacitidine for injection has the advantages of simple production process, low energy consumption, stable product quality and more suitable for commercial production.

DETAILED DESCRIPTION OF THE INVENTION

The following specific examples are given for further understanding the present invention, but the invention is not limited to the following examples.

Example 1

| Ingredients | amount |
| --- | --- |
| Azacitidine | 100.0 g |
| Mannitol | 100.0 g |
| Water for injection | 23 L |

Made a total of 1000 bottles

The preparation method comprises the following steps: 80% of the total volume of water for injection was measured, and the temperature was controlled at 2° C.; mannitol was added and stirred to completely dissolved, and the temperature was controlled at 2° C.; azacitidine was added and stirred to completely dissolved, and the temperature was controlled at 2° C.; after filtration, the resulting mixture was filled into penicillin bottles and partially stoppered; the above filled partially stoppered penicillin bottles were placed into a freeze-drier and pre-frozen at −35° C., and the temperature was maintained for 2 h; the temperature of the shelf was raised to −10° C. at a rate of 15° C./h and maintained for 15 h; then the temperature was raised to 30° C. at a rate of 20° C./h and maintained for 18 h; after nitrogen filling, stoppering, capping and packaging were performed to obtain a product.

Example 2

| Ingredients | amount |
| --- | --- |
| Azacitidine | 100.0 g |
| Mannitol | 100.0 g |
| Water for injection | 23 L |

Made a total of 1000 bottles

The preparation method comprises the following steps: 80% of the total volume of water for injection was measured, and the temperature was controlled at 4° C.; mannitol was added and stirred to completely dissolved, and the temperature was controlled at 4° C.; azacitidine was added and stirred to completely dissolved, and the temperature was controlled at 4° C.; after filtration, the resulting mixture was filled into penicillin bottles and partially stoppered; the above filled partially stoppered penicillin bottles were placed into a freeze-drier and pre-frozen at −35° C., and the temperature was maintained for 2 h; the temperature of the shelf was raised to −10° C. at a rate of 15° C./h and maintained for 15 h; then the temperature was raised to 30° C. at a rate of 20° C./h and maintained for 18 h; after nitrogen filling, stoppering, capping and packaging were performed to obtain a product.

Example 3

| Ingredients | amount |
| --- | --- |
| Azacitidine | 100.0 g |
| Mannitol | 100.0 g |
| Water for injection | 23 L |

Made a total of 1000 bottles

Note: The content of bacterial endotoxin in mannitol is 2.5 EU/g, and the content of bacterial endotoxin in azacitidine is 0.6 EU/mg.

The preparation method comprises the following steps: 80% of the total volume of water for injection was measured, and the temperature was controlled at 6° C.; mannitol was added and stirred to completely dissolved, and the temperature was controlled at 6° C.; azacitidine was added and stirred to completely dissolved, and the temperature was controlled at 6° C.; after filtration, the resulting mixture was filled into penicillin bottles and partially stoppered; the above filled partially stoppered penicillin bottles were placed into a freeze-drier and pre-frozen at −35° C., and the temperature was maintained for 2 h; the temperature of the shelf was raised to −10° C. at a rate of 15° C./h and maintained for 15 h; then the temperature was raised to 30° C. at a rate of 20° C./h and maintained for 18 h; after nitrogen filling, stoppering, capping and packaging were performed to obtain a product.

The characteristics, contents and related substances of products in Examples 1-3 were investigated at day 0 and 6 months at 40° C., respectively. The results are shown in the following table:

| | | Characteristics | Content/% | Related Substances | |
| --- | --- | --- | --- | --- | --- |
| | | | | Maximum Single Impurity | Total Impurity |
| Day 0 | Example 1 | white loose massive | 99.7 | 0.31 | 0.43 |
| | Example 2 | white loose massive | 100.1 | 0.29 | 0.41 |
| | Example 3 | white loose massive | 99.6 | 0.33 | 0.45 |
| 6 months after | Example 1 | white loose massive | 99.6 | 0.72 | 0.85 |
| | Example 2 | white loose massive | 99.9 | 0.69 | 0.82 |
| | Example 3 | white loose massive | 99.4 | 0.71 | 0.83 |

The above table shows that the azacitidine for injection has the same stability when the temperature for preparing the solution is 2° C., 4° C. and 6° C., respectively.

The detected result of the content of bacterial endotoxin in the prepared product of Example 3 is less than 1.2 EU/mg.

Example 4

| Ingredients | amount |
| --- | --- |
| Azacitidine | 100.0 g |
| Mannitol | 100.0 g |
| Water for injection | 23 L |

Made a total of 1000 bottles

The preparation method comprises the following steps: 80% of the total volume of water for injection was measured, and the temperature was controlled at 6° C.; mannitol was added and stirred to completely dissolved, and the temperature was controlled at 6° C.; azacitidine was added and stirred to completely dissolved, and the temperature was controlled at 6° C.; after filtration, the resulting mixture was filled into penicillin bottles and partially stoppered; the above filled partially stoppered penicillin bottles were placed into a freeze-drier and pre-frozen at −40° C., and the temperature was maintained for 2 h; the temperature of the shelf was raised to −10° C. at a rate of 15° C./h and maintained for 15 h; then the temperature was raised to 30° C. at a rate of 20° C./h and maintained for 18 h; after nitrogen filling, stoppering, capping and packaging were performed to obtain a product.

Example 5

| Ingredients | amount |
| --- | --- |
| Azacitidine | 100.0 g |
| Mannitol | 100.0 g |
| Water for injection | 23 L |

Made a total of 1000 bottles

The preparation method comprises the following steps: 80% of the total volume of water for injection was measured, and the temperature was controlled at 2° C.; mannitol was added and stirred to completely dissolved, and the temperature was controlled at 2° C.; azacitidine was added and stirred to completely dissolved, and the temperature was controlled at 2° C.; after filtration, the resulting mixture was filled into penicillin bottles and partially stoppered; the above filled partially stoppered penicillin bottles were placed into a freeze-drier and pre-frozen at −30° C., and the temperature was maintained for 2 h; the temperature of the shelf was raised to −10° C. at a rate of 15° C./h and maintained for 15 h; then the temperature was raised to 30° C. at a rate of 20° C./h and maintained for 18 h; after nitrogen filling, stoppering, capping and packaging were performed to obtain a product.

What is claimed is:
1. A preparation method of azacitidine for injection, wherein each injection vial of azacitidine for injection contains 100 mg of azacitidine and 100 mg of mannitol, the preparation method comprising the following steps:
 a. adding water for injection at a temperature of 2-6° C.;
 b. adding mannitol, and stirring to completely dissolve, at a temperature of 2-6° C.;
 c. adding azacitidine, and stirring to completely dissolve, at a temperature of 2-6° C., to obtain an azacitidine solution for injection, wherein upon completion of steps a) thru c), 80% of the volume of the azacitidine solution is water for injection, with the balance of the volume of the azacitidine solution being mannitol and azacitidine;

d. filling each injection vial with 23 ml of the azacitidine solution for injection after filtration;

e. freeze-drying at a preset temperature; and f. stoppering, capping and packaging after nitrogen filling.

2. The preparation method of azacitidine for injection according to claim 1, wherein the preparation method does not comprise a step of adsorbing with an activated carbon.

3. The preparation method of azacitidine for injection according to claim 1, wherein the azacitidine has a content of ≤0.6 Eu/mg of bacterial endotoxin.

4. The preparation method of azacitidine for injection according to claim 1, wherein the mannitol has a content of ≤2.5 Eu/g of bacterial endotoxin.

5. The preparation method of azacitidine for injection according to claim 1, wherein a prepared product of azacitidine for injection has a content of ≤1.2 Eu/mg of bacterial endotoxin.

6. The preparation method for azacitidine for injection according to claim 1, wherein the temperature for preparing a solution is controlled at 4-6° C.

7. The preparation method for azacitidine for injection according to claim 1, wherein the freeze-drying step comprises:

a. pre-freezing step: placing a sample into a shelf after a temperature of the shelf is reduced to −35±5° C. and maintaining the temperature for 2 hours;

b. first sublimation drying step: reducing vacuum degree to 50-150 μbar, raising the temperature of the shelf to −10° C. at a rate of 15° C./h, and maintaining the temperature for 15 hours; and c. second sublimation drying step: maintaining vacuum degree to 50-150 μbar, raising the temperature of the shelf to 30° C. at a rate of 20° C./h, maintaining the temperature for 18 hours, stoppering after nitrogen filling, and taking out from a freeze-drier.

* * * * *